United States Patent [19]

Koole

[11] Patent Number: 6,040,408
[45] Date of Patent: *Mar. 21, 2000

[54] RADIOPAQUE POLYMERS AND METHODS FOR PREPARATION THEREOF

[75] Inventor: Leo Hendrik Koole, Gulpen, Netherlands

[73] Assignee: Biomat B.V., Maastricht, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/793,620

[22] PCT Filed: Aug. 21, 1995

[86] PCT No.: PCT/NL95/00277

§ 371 Date: Apr. 10, 1997

§ 102(e) Date: Apr. 10, 1997

[87] PCT Pub. No.: WO96/05872

PCT Pub. Date: Feb. 29, 1996

[30] Foreign Application Priority Data

Aug. 19, 1994 [EP] European Pat. Off. ............... 94202363

[51] Int. Cl.⁷ ..................................................... C08F 18/00
[52] U.S. Cl. ....................... 526/292.1; 524/560; 524/561; 524/562
[58] Field of Search .......................... 526/292.1; 524/560, 524/561, 562

[56] References Cited

U.S. PATENT DOCUMENTS 4,644,025  2/1987  Sakagami et al. .
4,822,721  4/1989  Tsutsumi et al. ..................... 526/292.1
4,997,894  3/1991  Telgarden .
5,271,923  12/1993  Kochi et al. .

FOREIGN PATENT DOCUMENTS 0609156  9/1948  United Kingdom .
8201006  4/1982  WIPO ................................. 526/292.1

OTHER PUBLICATIONS

Answer 4 of 15, 1995:249908, Benzira et al "Strokes on a new radiopaque polymer biomaterial" Biomaterials, 15(14), 1122–8(English) 1994—in house abstract pp. 9–10.

Answer 5 of 15, 1995:132324, Dary et al "Novel aromatic dime thacrylate esters of dental resins" Mater. Med., 5(607), 350–2 (English) 1994—in house abstract pp. 10–11.

Answer 6 of 15 1994:708210, Kruft et al, "Two new radiopaque polymeric biomaterials" J. Biomed. Mater. Res., 28(11), 1259–66(English)1994—in house abstract pp. 11–13.

Answer 11 of 15, 1989:515854, Suzuki et al. Polym. Bull. (Berlin), 21(4), 415–20 (English) 1989. In house abstract pp. 21–24.

Hackh's Chemical Dictionary—May 27, 1981 p. 570.

*Primary Examiner*—Bernard Lipman
*Attorney, Agent, or Firm*—Welsh & Katz, Ltd.

[57] ABSTRACT

The invention is directed to a biomedical polymer having a number average molecular weight of at least 7.500, said polymer being substantially nonporous and having polymerized therein at least one monomer having at least one covalently bound iodine group.

5 Claims, No Drawings

RADIOPAQUE POLYMERS AND METHODS FOR PREPARATION THEREOF

The present invention relates to a class of polymeric materials exhibiting radiopacity due to the fact that molecules containing covalently-bound iodine were built-in during polymerisation. Fields of application of such radiopaque polymers include, but are not limited to: medical materials (e.g. bone cements, catheters, and implants such as blood vessel prostheses and endovascular stents); veterinary materials (e.g. implants, catheters), and toys, especially small objects with the associated danger of being swallowed. Due to the presence of covalently bound iodine in the polymer post-operative assessment of the fate of implants, using X-ray scanning, is possible.

In the literature some experiments have been described, dealing with the polymerization of iodine containing monomers. These experiments did not result in any suitable materials, as the polymerization did not proceed to a sufficient high molecular weight, or the resulting material did possess hemolytic properties, which makes the material unsuitable for biomedical applications, The present invention relates to a class of radiopaque biomedical polymeric materials having a number average molecular weight of at least 7500. These radiopaque materials are either: (i) polymers of a monomer molecule that contains covalently-bound iodine, or (ii) copolymers in which at least one of the different monomers contains covalently-bound iodine, or (iii) terpolymers or polymers of even higher complexity, in which at least one of the different monomers contains covalently-linked iodine.

This group of polymers encompasses a wide variety of materials since a virtually unlimited variation is possible for iodine containing monomers. Furthermore, the composition of copolymers, terpolymers, and other polymers such as mentioned under (ii) and (iii) can be varied, both in terms of relative concentration, and in terms of molecular structure of the different constituents.

Radiopaque polymers according to this invention are clearly distinguished with respect to prior art ("Preparation and evaluation of radiopaque hydrogel microspheres based on pHEMA/iothalamic acid and pHEMA/iopanoic acid as particulate emboli" A. Jayakrishnan et al., *Journal of Biomedical Materials Research*, 24, 993–1004 (1990); "Synthesis and polymerization of some piodpine-containing monomers for biomedical applications" A. Jayakrishnan et al., *Journal of Applied Polymer Science* 44, 743–748 (1992)) in which it was reported that only low-molecular-weight products are obtained when acrylic derivatives of tri-iodophenyl or iodothalamic acidare copolymerised with methyl methacrylate (MMA) or 2-hydroxyethyl methacrylate (HEMA).

The invention is explained in detail in the following: Although radiopaque polymers of different structural types are subject to this invention, the most predominant ones are polyacrylates and derivatives thereof. Preparation of radiopaque polyacrylates starts with synthesis of a monomer in which iodine is covalently bound. Molecules of this type include, but are not limited to the group of structures represented in Scheme I, which is divided into three subgroups (a, b, and c).

SCHEME I

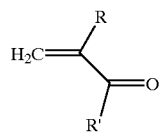

subgroup a.: iodine in group R'.
R=H, $CH_3$, $C_2H_5$, or another organic substituent.
R'=I, O—$C_6H_4$I, O—$C_6H_3I_2$, O—$C_6H_2I_3$, NH—$C_6H_4$I, NH—$C_6H_3I_2$, NH—$C_6H_2I_3$, O—$CH_2$—$CH_2$—C(O)—$C_6H_4$I, O—$CH_2$—$CH_2$—O—C(O)—$C_6H_3I_2$, O—$CH_2$—$CH_2$—O—C(O)—$C_6H_2I_3$, NH—$CH_2$—$CH_2$—C(O)—$C_6H_4$I, NH—$CH_2$—$CH_2$—O—C(O)—$C_6H_3I_2$, NH—$CH_2$—$CH_2$—O—C(O)—$C_6H_2I_3$, or another organic iodine-containing substituent.

subgroup b.: iodine in group R:
R=I, $CH_2$I, $CHI_2$, $CI_3$, or another organic iodine-containing substituent.
R'=$OCH_3$, O—$C_6H_5$, O—$CH_2$—$CH_2$—OH, O—$C_nH_{2n+1}$, or other organic groups.

subgroup c.: other organic molecules containing at least one polymerizable double bond and one or more covalently linked iodine atoms are present in the structure.

The first method of preparation of monomers in subgroup a. of Scheme I starts our with an acylic acid chloride., e.g. methacryloyl chloride. These reactive compounds can be coupled to a variety of iodine-containing alcohols, in a reaction in which hydrogen chloride is formed along with the product. As an example, reaction of methacryloyl chloride with 4-iodophenol in the presence of a base (triethylamine) yields (4-iodophenyl) methacrylate. The latter compound clearly belongs to subgroup a in Scheme I. A variety of analogous monomers can be prepared according to this method. The only essential requirement is that one or more iodine atoms must be present in the alcohol. Use of an iodine containing amine instead of the alcohol will generate an amide bond. For example: reaction of methacryloyl chloride with 4-iodo-aniline in the presence of a strong base will lead to (4-iodophenyl) methacrylamide which also belongs to subgroup a. in Scheme I. Amides, derived from an acrylic acid chloride and an iodine-containing amine are explicitly included in subgroup a. of Scheme I.

The second method for generating compounds from subgroup a. in Scheme I starts our with an acrylate that is available, for instance from a commercial source. The acrylate is treated with an excess of an iodine-containing alcohol. Such a procedure leads to cleavage Of the ester bond in the acrylate, and subsequently to substitution of the side-chain by the iodine containing group (trans-esterification). For example, methyl methacrylate can be treated with excess 4-iodophenol, and this reaction then affords 4-(iodophenyl) methacrylate. As said, the latter compound belongs to subgroup a. in Scheme I. The reaction can also be carried out with an iodine-containing amine, instead of the iodine-containing alcohol; an amide bond is generated in this case.

The third method for synthesising monomers of subgroup a. in Scheme I. is based on coupling of an acrylic compound with a free hydroxyl group or a free amino group, with an iodine-containing carboxylic acid. Two examples illustrate this approach. The first example relates to reaction of 2-hydroxyethyl methacrylate (HEMA) with 4-iodocarboxylic acid. This reaction, a normal esterification, can be carried out in many ways. It has been observed by the inventors that the reaction proceeds with excellent yield in the presence of N,N'-dicyclohexyl carbodiimide (DCC). Special care should be taken to isolate the product in pure form, i.e. to quantitatively remove the side product N,N'-dicyclohexyl urea. The second example relates to the analogous reaction of 2-aminoethyl methacrylate with 4-iodocarboxylic acid. This reaction also proceeds in the presence of DCC. Products obtained in reactions according to both examples belong to subgroup a. in Scheme I.

The fourth method of synthesis of monomers Of subgroup a. in Scheme I is based on coupling of acrylate molecules with a free hydroxyl-, amino-, or other reactive nucleophilic group, with an iodine-containing acid chloride. In fact, this approach is the opposite of the first method of synthesis (vide supra). The procedure for executing the fourth method is therefore identical to the procedures for executing the first method.

Molecules belonging to subgroup b. in Scheme I. can be prepared according to prior art.

Molecules belonging to subgroup c. in Scheme I are iodine-containing congeners of molecules that are known to readily take part in copolymerisations with acrylates. For example, it is well known that styrene, N-vinyl-2-pyrollidone, or vinylacetate readily react with MMA, and/or HEMA in radical polymerisation reactions. Molecules in subgroup c. therefore include, but are not limited to, the structures in the attached Scheme II.

Polymer Synthesis.

Two procedures for preparation of radiopaque acrylate polymers are disclosed. One method refers to synthesis in bulk, the other method refers to synthesis in solution. In the bulk procedure, an iodine-containing monomer (viz. Scheme I) is mixed with one or more other reactive monomers (e.g. MMA, HEMA, styrene), an initiator (e.g. molecules with the property of undergoing homolytic bond cleavage upon raising the temperature, e.g. acyl peroxides, cumyl- or tert. butyl peroxides, tetrazenes, AIBN, also: reagents that can be used in photopolymerisations, redoxinitiation), and a chain-transfer agent (e.g. mercapto ethanol). The reaction mixture is transferred into a Teflon tube which is tightly closed with a glass stopper on one end. The tube is then subjected to a controlled heat treatment. This affords the radiopaque materials as transparent glassy rods.

In the solution procedure, an iodine-containing monomer (viz. Scheme I) is mixed with one or more other reactive monomers (e.g. MMA, HEMA, styrene), an initiator (vide supra), and a chain-transfer agent (e.g. mercapto ethanol). This mixture is dissolved in a clean, high-boiling solvent (e.g. dimethylformamide, dimethyl-sulfoxide). The resulting solution is stirred continuously and subjected to a controlled heat treatment. After work-up, this renders a radiopaque polymer as a white solid. Work-up can be cumbersome, since removal of the last traces of high-boiling solvent is often difficult. Pure product can be obtained after repeated washing steps, and lyophilisation.

With respect to the polymers that were obtained according to both procedures, it was found that a content of ca. 20 mol % of iodine-containing monomer ensures sufficient visibility using clinically common imaging techniques based on X-ray absorption. Thin fibers of materials as described above (content of iodine-containing monomer ca. 20 mol %) were clearly visible under routine fluoroscopy, even when a correction was applied for X-absorption due to the human body (a 15-cm thick layer of PMMA glass was placed in the X-ray beam). It must be noted that the content of 20 mol % refers to monomers with one iodine per molecule. Evidently, use of a monomer with two (three) iodine atoms per molecule will lead to clear visibility at a content of only 10 (7) mol %.

The polymers of the present invention can, as has been indicated above, be used for various biomedical purposes, which means that they have to be compatible in the human or animal body. More in particular suitable biomedical materials do not possess hemolytic properties. More in particular the materials according to the invention are suitable as bone cements, catheters, and implants such as blood vessel prostheses and endovascular stents (in general medical materials); veterinary materials (e.g. implants, catheters), and toys, especially small objects with the associated danger of being swallowed.

The invention also relates to a monomer mixture that is suitable for preparing a biomedical polymer containing covalently bound iodine, said monomer mixture comprising at least one monomer having at least one iodine group covalently bound thereto, at least one reaction initiator and/or catalyst, optionally one or more other monomers not containing iodine and fillers. Preferably said monomer mixture is provided in the form of a two-pack system that is suitable for in-situ use, for example as bone cement, as dental filling material, or as biomedical construction material.

The invention is elucidated on the basis of the following examples that are not intended to restrict the invention.

EXAMPLES

Example 1

Polymers A, B and C were prepared using the bulk polymerization method, the composition of the polymers is as follows:

Polymer A: 80 mol % MMA, 20 mol % [4-iodophenyl] methacrylate;

Polymer B: 65 mol % MMA, 15 mol % HEMA, 20 mol % [4-iodophenyl]methacrylate;

Polymer C: 60 mol % MMA, 19 mol % HEMA, 21 mol % 2-[4-iodobenzoyl]ethyl methacrylate.

Some physico-chemical data on these polymers are summarized in Table I.

TABLE I

Physico-chemical properties of some iodine-containing radiopaque polymers.

| Pol[1] | Mw[2] | Mn[2] | Xray -visibility[3] | contact angle[4] | purity check[5] | monomer content |
|---|---|---|---|---|---|---|
| A | 61.5 | 22.7 | ++ | 52.4 | NMR, GPC | <1% |
| B | 41.3 | 12.2 | ++ | 43.1 | NMR, GPC | <1% |
| C | 43.1 | 7.9 | ++ | 42.8 | NMR, GPC | <1% |

[1] Polymer A: 80 mol % MMA, 20 mol % [4-iodophenyl]methacrylate; Polymer B: 65 mol % MMA, 15 mol % HEMA, 20 mol % [4-iodophenyl] methacrylate; Polymer C: 60 mol % MMA, 10 mol % HEMA, 21 mol % 2-[4-iodobenzoyl]ethyl methacrylate.
[2] Determined by gel permeation chromatography, using polystyrene standards; expressed in kg/mol.
[3] Visibility under routine fluoroscopy, adsorption of X-rays due to surrounding bone and tissue mimicked by 15 cm of Plexi glass.
[4] Measured according to the dynamic Wilhelmy plate technique; listed data are receding contact angles, expressed in degrees.
[5] Proton NMR measurements at 400 MHz, measured on solutions of polymers A–C in DMSO solution.

Some biochemical data on these polymers are summarized in Table II.

TABLE II

Biochemical properties of some iodine-containing radiopaque polymers.

| Polymer[1] | Clotting time[2] | platelet adhesion[3] | platelet morphology[3] |
|---|---|---|---|
| A | 392 | 10% | unchanged |
| B | 553 | no | — |
| C | 700 | 10% | spreaded |

[1] See legend Table 1.
[2] Measured in a routine thrombin generation test procedure, expressed in seconds.
[3] Determined by scanning electron microscopy. Polymers B and C were designed such that they combine X-ray visibility with enhanced biochempatibility. This is a unique feature.

Example 2

A copolymer, composed of methylmethacrylate (MMA, 51 mole %), and 2-[2'-iodobenzoyl] ethylmethacrylate (49 mole %), was prepared in a typical bulk synthesis (vide supra). The material showed Mw=80.000 and Mn=36000 (GCP analysis) while the residual monomer content was substantially smaller than 1%. The material was first granulated and subsequently powdered. The powder was then thoroughly mixed with polymethylmethacrylate (pMMA) powder, in the ratio 1:8 (w/w). A peroxide was added in the ratio 1:200 (w/w). The resulting powder was used to replace the solid component of a commercial bone cement kit. The commercial liquid bone cement component was mixed with the powder. This yielded a cement, which hardened in 10–20 minutes. Mechanical tests of the material revealed that the tensile strength of the cement containing the radiopaque copolymer is 58 MPa, which is substantially larger than that for the commercial bone cement (48 MPa). The commercial bone cement was made radiopaque through addition of 10% (by weight) of barium sulfate. Apparently, the addition of barium sulfate (which does not mix with the polymeric cement matrix, and tends to form clumps) in fact weakens the cement. This problem can be solved via the use of a radiopaque (copolymer) as described in this example. Moreover, leaching a toxic barium sulfate cannot occur with the proposed new cement.

I claim:

1. A toy or bone cement being prepared from a radiopaque polymer, said polymer having an average molecular weight of at least 7500, and being substantially non-porous and having polymerized therein at least one monomer having at least one but not more that two covalently bound iodine groups, said monomer having the formula

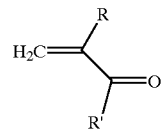

wherein R=H, $CH_3$, $C_2H_5$, or another organic substituent, and R'=O—$C_6H_4I$, O—$C_6H_3I_2$, NH—$C_6H_4I$, NH—$C_6H_3I_2$, O—$CH_2$—$CH_2$—C(O)—$C_6H_4I$, O—$CH_2$—$CH_2$—O—C(O)—$C_6H_3I_2$, NH—$CH_2$—$CH_2$—C(O)—$C_6H_4I$ or NH—$CH_2$—$CH_2$—O—C(O)—$C_6H_3I_2$.

2. The toy or bone cement of claim 1, wherein at least 20% of the number of polymerized monomers contains said covalently bound iodine.

3. The toy or bone cement of claim 1, wherein said monomer having iodine covalently bound is a reactive monomer having an iodine containing group attached thereto after polymerization.

4. The toy or bone cement of claim 2, wherein said monomer having iodine covalently bound is a reactive monomer having an iodine containing group attached thereto after polymerization.

5. A toy or bone cement being prepared from a polymer, said polymer being a copolymer selected from the group consisting of a first copolymer comprising a mixture of methylmethacrylate and (4-iodophenyl) methacrylate;

a second copolymer comprising a mixture of methylmethacrylate, 2- hydroxy ethyl methacrylate, and (4-iodophenyl) methacrylate; and a. third copolymer comprising methylmethacrylate, hydroxy ethylmethacrylate and 2-(4-iodobenzoyl) ethylmethacrylate.

* * * * *